United States Patent
Gumbrell

(10) Patent No.: US 9,808,635 B2
(45) Date of Patent: Nov. 7, 2017

(54) ENVIRONMENT AND USE MONITORING SYSTEM FOR ADVANCED LIFE SUPPORT DEVICES

(71) Applicant: KONINKLIJKE PHILIPS N.V., Eindhoven (NL)

(72) Inventor: George Paul Gumbrell, Worcester, MA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/424,189

(22) PCT Filed: Aug. 23, 2013

(86) PCT No.: PCT/IB2013/056841
§ 371 (c)(1),
(2) Date: Feb. 26, 2015

(87) PCT Pub. No.: WO2014/033605
PCT Pub. Date: Mar. 6, 2014

(65) Prior Publication Data
US 2015/0321020 A1    Nov. 12, 2015

Related U.S. Application Data

(60) Provisional application No. 61/694,426, filed on Aug. 29, 2012.

(51) Int. Cl.
*A61N 1/39* (2006.01)
*A61N 1/372* (2006.01)

(52) U.S. Cl.
CPC ........ *A61N 1/3925* (2013.01); *A61N 1/37282* (2013.01)

(58) Field of Classification Search
CPC .......................... A61N 1/3925; A61N 1/37282
See application file for complete search history.

(56) References Cited

U.S. PATENT DOCUMENTS

| | | |
|---|---|---|
| 5,097,830 A | 3/1992 | Eikefjord et al. |
| 5,342,403 A | 8/1994 | Powers et al. |
| 5,571,141 A | 11/1996 | McNeil et al. |
| 5,964,786 A | 10/1999 | Ochs et al. |
| 7,243,270 B2 | 7/2007 | Taniguchi et al. |

(Continued)

FOREIGN PATENT DOCUMENTS

| | | |
|---|---|---|
| CN | 101534902 A | 9/2009 |
| CN | 101972508 A | 2/2011 |

(Continued)

*Primary Examiner* — Rex R Holmes

(57) ABSTRACT

A data collection device (100) is described which monitors the environmental conditions and the operations of a medical device (10). The data collection device may be arranged to communicate wirelessly via a cloud computing environment with a central computer (210). The central computer compares the reported use data with a preventive maintenance model to predict when or how the medical device will fail. In addition, the central computer may integrate reports from many data collection devices operating in various environments for the purpose of analyzing and improving the predictive maintenance model.

17 Claims, 6 Drawing Sheets

(56) References Cited

U.S. PATENT DOCUMENTS

| | | | |
|---|---|---|---|
| 2004/0122294 A1* | 6/2004 | Hatlestad | A61B 5/0031 600/300 |
| 2004/0214148 A1 | 10/2004 | Salvino et al. | |
| 2006/0149323 A1 | 7/2006 | Merry et al. | |
| 2010/0292544 A1 | 11/2010 | Sherman et al. | |
| 2012/0124129 A1 | 5/2012 | Klimentiev et al. | |
| 2012/0203084 A1 | 8/2012 | Li et al. | |

FOREIGN PATENT DOCUMENTS

| | | |
|---|---|---|
| JP | 2005319322 A | 11/2005 |
| JP | 2007058442 A | 3/2007 |
| WO | 9400182 A2 | 1/1994 |

\* cited by examiner

ENVIRONMENT AND USE MONITORING SYSTEM FOR ADVANCED LIFE SUPPORT DEVICES

This application is a national stage application under 35 U.S.C. §371 of International Application No. PCT/IB2013/056841 filed on Aug. 23, 2013 and published in the English language on Mar. 6, 2014 as International Publication No. WO 2014/033605 A1, which claims priority to U.S. Application No. 61/694,426 filed on Aug. 29, 2012, the entire disclosures of which are incorporated herein by reference.

The invention relates generally to an improved apparatus and method for capturing information related to the environmental conditions and use experienced by a medical device. The information is used to modify the protocol for maintaining the medical device if necessary. In an illustrated embodiment, the invention is incorporated with an external defibrillator having a built-in self testing routine. Information is collected and conveyed to a central computer. The central computer may further integrate the use information from a number of similar devices. If necessary, the central computer adjusts the self testing routine or inspection protocol based on the information.

Real world environmental conditions such as temperature, humidity, condensation, shock, and vibration have been known for some time to be directly related to product reliability issues. Standard acceleration models have been used to simulate real world conditions for the purpose of improving product designs and for reducing field failures. However, these acceleration models merely simulate real world conditions. Because real world conditions are often different from the simulation, the models are error-prone.

Reliability is especially important in the case of medical products, where a failure during use can have catastrophic consequences to the patient and/or the user. For this reason, many existing medical devices automatically record a history of use for later retrieval and analysis. The use history can be used by the manufacturer to improve later product designs, to modify device operating protocols, and sometimes to initiate corrective actions in the deployed device population. Internal use histories may also be supplemented with manual logs filled out by the user.

One prior art invention which automatically adjusts a self-test in accordance with temperature changes near the device is described in U.S. Pat. No. 5,964,786, entitled "Environment-Responsive Method for Maintaining an Electronic Device." The patent is incorporated herein by reference. The defibrillator described therein utilizes an internal self-testing protocol in which the self-test schedule is automatically adjusted based on changes in the device temperature.

The existing methods for exploiting such real-world use information are sub-optimal. Internal use histories must await the return of the product either to the medical administrator or the manufacturer for retrieval. The methods of retrieval are often difficult, invasive, limited in sample size, and delayed for long periods of time from the time of use. Manual records can also be error prone due to user bias in the knowledge that the particular device is being monitored. For this reason, an improved method and apparatus are needed to timely collect and respond to the use environment experienced by the population of medical devices.

Similarly, what is needed is an improved method for maintaining a medical device, one which is responsive to the particular environment in which the device is used. For example, external defibrillators are exposed to a wide range of use environments. Some defibrillators are used in a simple hospital environment, where temperature and other conditions are relatively constant and where the defibrillator is relatively stationary. Other defibrillators of the exact same model, however, are deployed in mobile environments such as Emergency Medical Services (EMS) vehicles, fire trucks, or military first aid, where the defibrillators are exposed to extremely harsh environmental conditions and rough handling. A method of adjusting the self-testing and maintenance protocols according to the use environment would improve the device reliability, while also avoiding unnecessary maintenance activities. In addition, adjusting the internal self-testing protocol would optimize battery life by avoiding aggressive self-testing activities that may be unnecessary for a benign use environment.

In accordance with the principles of the present invention, an improved device and method for monitoring the use history of a medical device is described. The monitoring may comprise use and environment information, which can in turn be used to provide customized preventive maintenance feedback to the device. Thus, the invention incorporates mission-critical data and architecture, in particular for defibrillators and other advanced life support devices, which monitors in real-time or near real-time before the device fails, in order to provide customized preventive maintenance feedback to the end user. This data would be also used to enhance future product designs.

It is another object of the invention to describe a system which incorporates a medical device, or plurality of medical devices, each in communication with a central computer. The system is operable to compare environmental data and operating data against a predictive maintenance model, and to predict a time to failure of the device based on the comparison. The system is further operable to provide a feedback to the device according to the comparison. The system may also be enabled to adjust the predictive maintenance model based on the collected use history.

A particular object of the invention is to describe a network for the collection of real-time or near real-time mission critical data and environmental data from a population of medical devices. The collection is for the purpose of developing predictive failure models over the entire product population so that customized preventive maintenance feedback can be given to the end user. In addition, the collection can be used to enhance future product designs for defibrillators and other advanced life support devices.

It is yet another object of the invention to describe an improved method for monitoring the use history of a medical device, and for using the monitoring to adjust an operational condition of the medical device based on a comparison with a pre-determined maintenance model. The method can be applied in quiescent periods so as not to interrupt critical care to the patient.

Exemplary embodiments according to the present disclosure are further described herein below with reference to the appended figures. While some exemplary embodiments may be described separately from one another (e.g., for ease of presentation and understanding), one having ordinary skill in the art shall appreciate in view of the teachings herein that such exemplary embodiments can be used independently and/or in combination with each other. Indeed, the implementation and use of the exemplary embodiments described herein, including combinations and variations thereof all of which are considered a part of the present disclosure, can depend on, e.g., particular clinical and/or field use/application, integration with other related technologies, available resources, environmental conditions, etc. Accordingly, nothing in the present disclosure should be interpreted as limiting of the subject matter disclosed herein.

The present disclosure will present in detail the following description of preferred embodiments which should be considered in view of the appended figures, as referenced herein below, for example.

The present invention is further described in three main elements as exemplary embodiments of the present invention. For example, the first element comprises an apparatus that is co-located with the medical device. The apparatus and medical device interact to collect the use history of the device, such as button pushes, detailed hardware and software error logs, power fluctuations, charge times, and key patient parameters. In addition, the apparatus incorporates sensors which collect environmental data such as temperature, humidity, condensation, shock, vibration, and location. The apparatus further incorporates a communications feature for conveying the data to a computer for further analysis.

The second exemplary element of the invention is a communications pathway to the analyzing computer. The computer may be disposed at a central location, i.e. a central computer. The communications pathway may be constructed as a network, such as a cloud computing network. The network may be disposed to wirelessly collect and store patient and other information at a storage location, for future retrieval and analysis by authorized users.

The third exemplary element of the invention is for analysis and feedback. The use data and environmental data are compared to a predictive maintenance model which resides on a computer. If the data departs sufficiently from the model, the computer may issue a command to adjust an operational condition of the medical device. If the computer is a central computer, the command is communicated to the device via the network. The device operations may then be automatically adjusted in some way. For example, a self-testing schedule may be adjusted to test the device more often if it is subjected to an extreme environment or use schedule. Or a message may be displayed on the device to inspect the device more frequently, or even to remove it from service and return to the manufacturer. Finally, the data itself may provide a catalyst to modify the predictive maintenance model itself, by correlating failure profiles with the actual device use model. If, for example, devices fail less often in extremely cold temperatures than forecast during design, then the allowable temperature operating range could be expanded.

Figure 1:
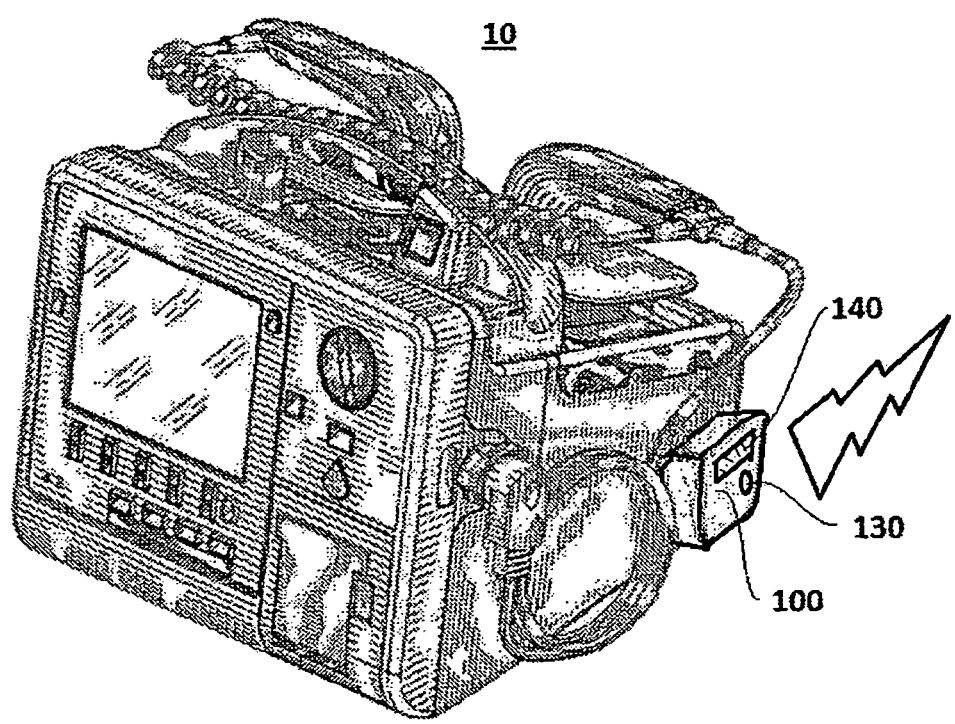
FIG. 1 is an illustration of an external defibrillator for use with the present invention.

Now turning to the drawings, FIG. 1 illustrates one embodiment of a medical device 10 disposed with a data collection device 100. In the illustrated embodiment, medical device 10 is an external defibrillator, such as the Heartstart XL+™ manufactured by Philips Healthcare, Andover Mass.

FIG. 1 shows data collection device 100 as attached to and external to device 10. The attachment may be by a clip such that the devices may be detached from each other, or may be screwed or permanently affixed together. This configuration is advantageous because data collection device 100 can be powered by its own rechargeable or replaceable power supply, such that the medical device 10 power supply is reserved solely for use in medical treatment events. As illustrated, data collection device 100 may optionally include a user output 140 which is a display. User output 140 may also be disposed as an indicator light, a readiness indicator, or as an audible annunciator.

Data collection device 100 may also comprise a wireless transceiver 130. Transceiver 130 is preferably disposed to transmit use data collected by the device 10 and/or monitor 100 as well as environmental data collected by monitor 100. Transceiver 130 may also be disposed to receive instructions which automatically modify an operational status of device 10. In consequence of the receiving, a message or indication may be placed on user output 140 or on a user output of device 10. A message may indicate that an additional inspection of the device is necessary, that the device should be removed from service, or that the device should be returned to the manufacturer. Preferably, the indication occurs prior to any failure of device 10. In another embodiment, a self-testing protocol residing within device 10 is adjusted via monitor 100 to reflect the actual operating environment experienced by the device.

In an alternate embodiment, data collection device 100 is incorporated within the device 10 housing in order to realize cost and simplicity benefits of sharing common components, such as displays, controls, annunciators, or power sources.

Figure 2:
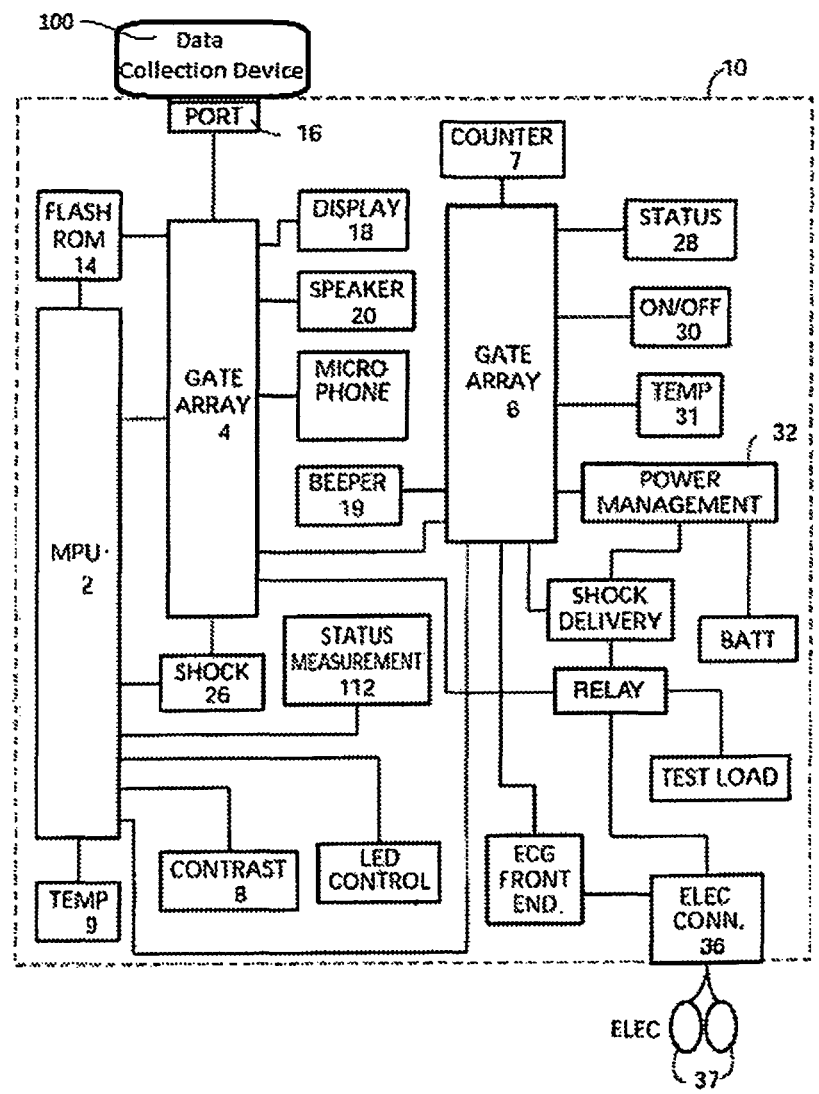
FIG. 2 is a block diagram showing the functional components of an external defibrillator that may be used to implement the methods of this invention.

Turning now to FIG. 2, shown is a block diagram showing an external defibrillator that may be used to implement the methods of this invention. Some of the FIG. 2 elements shown bear only indirectly to the present invention, and are included solely to show one context in which the invention may operate.

Device 10, here exemplified as an external defibrillator is shown in FIG. 2. While defibrillators are particularly appropriate for implementing this invention, the invention is not limited to use in defibrillators. Defibrillators provide electrotherapy treatment for sudden cardiac arrest by providing a high-voltage shock through a patient's heart via externally-applied electrodes 37. An electrical connector 36 permits connection of disposable electrodes to device 10.

In the defibrillator shown in FIG. 2, battery capacity tests are run daily as part of a suite of automatic self-tests via power management block 32, and the results are recorded in a device history log (DHL) stored in memory 14. Other device 10 functions are tested or measured at status measurement 112 and recorded in memory 14. Device 10 also periodically records temperature into the DHL via temperature sensors 9 or 31. Control functions of device 10 are distributed among a main processor unit (MPU) 2 and two gate arrays 4 and 6. Gate array 6 also performs some of the functions of the self-test initialization generation.

The self-testing features of device 10 extend to connected accessories as well. The defibrillator, for example, may include pre-connected disposable electrodes 37 which are checked for continuity by the self-testing protocol. Advanced defibrillator/monitors, for example, may include a module for monitoring electrocardiograms (ECG), blood oxygen (SPO2) or non-invasive blood pressure (NIBP), either hardwired to the defibrillator or wirelessly connected. Device 10 is envisioned to include features that automatically check these features, and/or their connecting cables, on a periodic basis.

Gate array 6 may monitor "wake-up" conditions, such as an out-of-bounds temperature reading at temperature sensor 31, the press of an on/off button 30 by the user, or a detected drop/shock experienced by the device. Gate array 6 may also blink a status ready indicator light 28 or beeper 19 periodically to indicate the operational status of the device 10. Gate array 6 may also track the number of button presses, turn-on/off, shocks delivered, and other user actions at counter 7, also stored in memory 14.

MPU 2 acts as the general controller of device 10 when it is operating outside of the standby mode. MPU 2 controls the decision whether to shock via block 26. MPU 2 also provides user control functions for a device display 18 via contrast button 8. Gate array 4 provides display 18 functionality and issues aural commands via speaker 20.

Taken together, the components of device 10 form a self-test circuit for sensing a fault in the device. The components also provide visual and audio outputs for indicating the status of the device and for issuing instructions to the user. The controller functions to collect and record operating data, and to execute software instructions for conducting the self-test.

The operation of device 10 is also influenced by data collection device 100 via port 16. Port 16 operates to communicate use data, such as stored in the DHL, from device 10 to data collection device 100. Port 16 also operates to communicate instructions and environmental data from monitor 100 to device 10. The instructions are used by MPU 2 to adjust device 10 operations, such as to display a message on display 18 or to adjust a timing or test parameter of the self-testing algorithm.

Figure 3:
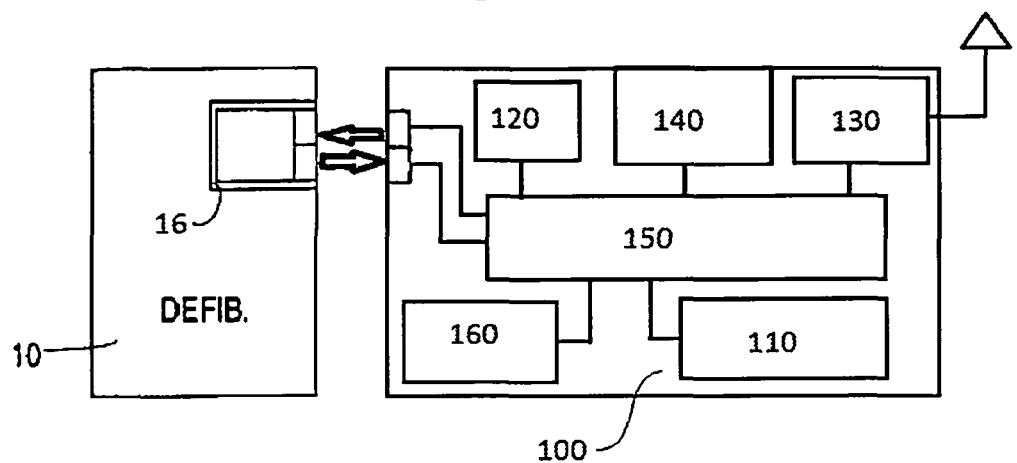
FIG. 3 is a functional block diagram of an external defibrillator and the inventive data collection device, with one embodiment of a communications interface.

FIG. 3 illustrates a functional block diagram of the data collection device 100 disposed as interfaced with device 10. Port 16 is shown as a bidirectional communication port which interfaces with monitor 100. The interface can be any commonly known in the art, such as infrared, radio, Bluetooth™ or b-field communications protocols.

Device 100 is comprised of several functional circuits. One or more environmental sensors 110 operate to collect environmental data, such as temperature, humidity, condensation, shock, or vibration. Another sensor 110 embodiment is a GPS sensor which provides location data of the device. One or more of these sensors can be disposed within device 10 as well.

Environmental data collected by sensor(s) 110 is stored in a data collection device memory 120. The data is preferably correlated in time, and also is preferably combined with operating data obtained from the medical device 10 via port 16.

The environmental data and operating data is disseminated via wireless transceiver 130 in a preferred embodiment. Transmission of the data is preferably on a scheduled basis. Transceiver 130 may also be operable to receive instructions from a remote transmitter, such as an instruction to modify a device maintenance routine. The received instruction is communicated to device 10 via port 16.

An optional user output 140 may be disposed on the outside of data collection device 100, for conveying information to the user about the device. Output 140 may be responsive to the instructions to provide a message or indication light to the user to provide some preventive maintenance feedback which is in addition to the previously-provided maintenance protocol. Output 140 may also be disposed as a warning light or an audible beeper to attract the attention of maintenance personnel to a message displayed on device 10 itself.

All functions of data collection device 100 are controlled by a controller 150, which is in communication with each of the sensor 110, memory 120, output 140, port 16, and wireless transceiver 130. Controller 150 may communicate any received instructions to medical device 10 for the purpose of causing an alteration in the self-test protocol of device 10, or to display a message there. Power supply 160 provides power, independent of device 10, to the data collection device 100.

Figure 4:
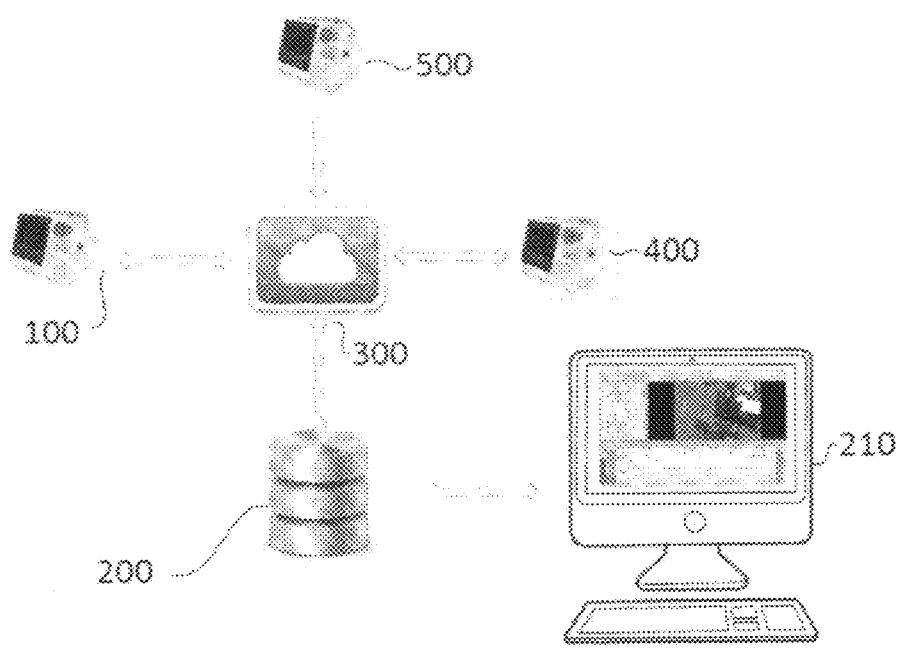
FIG. 4 illustrates the inventive system comprising a plurality of medical devices in communication via a cloud computing environment with a central computer.

FIG. 4 illustrates a system for monitoring the use history and the environmental history of one or more medical devices, each device having a data collection device 100, 400, 500. The medical devices are preferably similar in configuration to each other, such that the same preventive maintenance model would apply to each device. Each medical device and associated data collection device 100, 400, 500 are disposed as described above and as shown in FIGS. 1 through 3. Namely, each of the medical devices has a self-test circuit for sensing a fault in the device and a communications path for communicating with a data collection device. Memory in each data collection device is operable to record operating data from the medical device and environmental data collected by an environmental sensor in the monitor. Each monitor has a wireless transceiver operable to transmit and receive data. Each of the monitors is controlled by a controller, which causes the monitor to transmit the environmental and operating data during periods prior to a sensed fault in the attached medical device.

The FIG. 4 system includes a communications pathway, such as a cloud communication environment 300, which links each monitor 100, 400, 500 with a remote second memory 200. Second memory 200 receives and stores environmental data and operating data from each of the devices, for later analysis and comparison against a preventive maintenance model. A central computer 210 is further arranged to access the data stored in memory 200, preferably via cloud communication environment 300 as well. Central computer 210 executes predictive maintenance model software, which compares the environmental and operating data obtained from memory 200 with parameters in the maintenance model.

The predictive maintenance model may be configured to compare real-world environmental and operating conditions as experienced by the devices with design parameters established during design of the devices. The output of the comparison is preferably a prediction of the time to failure of the device, and perhaps the mode of failure as well.

If the predicted time to failure falls within a pre-determined limit, central computer 210 may transmit an alert back to the data collection device 100, 400, 500 via the cloud communication environment 300. The particular data collection device may then communicate with the attached medical, device to cause the device to adjust a parameter in its self-test circuit for the purpose of enhancing the self-test (s) corresponding to the impending device failure. In addition, the data collection device may issue or cause to issue a user alert on a user output disposed on the monitor or the device. The user alert may comprise an instruction to alter the existing preventive maintenance protocol or to remove the device from service.

By incorporating real-world experience, data from multiple devices and data collection devices that are operating in a variety of environments, the FIG. 4 system can realize additional advantages. First, the incidence of failure or not with regards to environments at the bounds of the predictive maintenance model limits may allow for the adjustment of the model in order to improve failure predictions. Also, the data may allow for improved characterization of the medical device performance within certain operating environments. For example, a particular device may be shown to perform better in high use environments than in high standby environments. With the improved knowledge of how the device operates in certain environments, the predictive maintenance model can also be refined and improved by adjusting the limit parameters for devices identified as operating in those particular environments.

Figure 5:
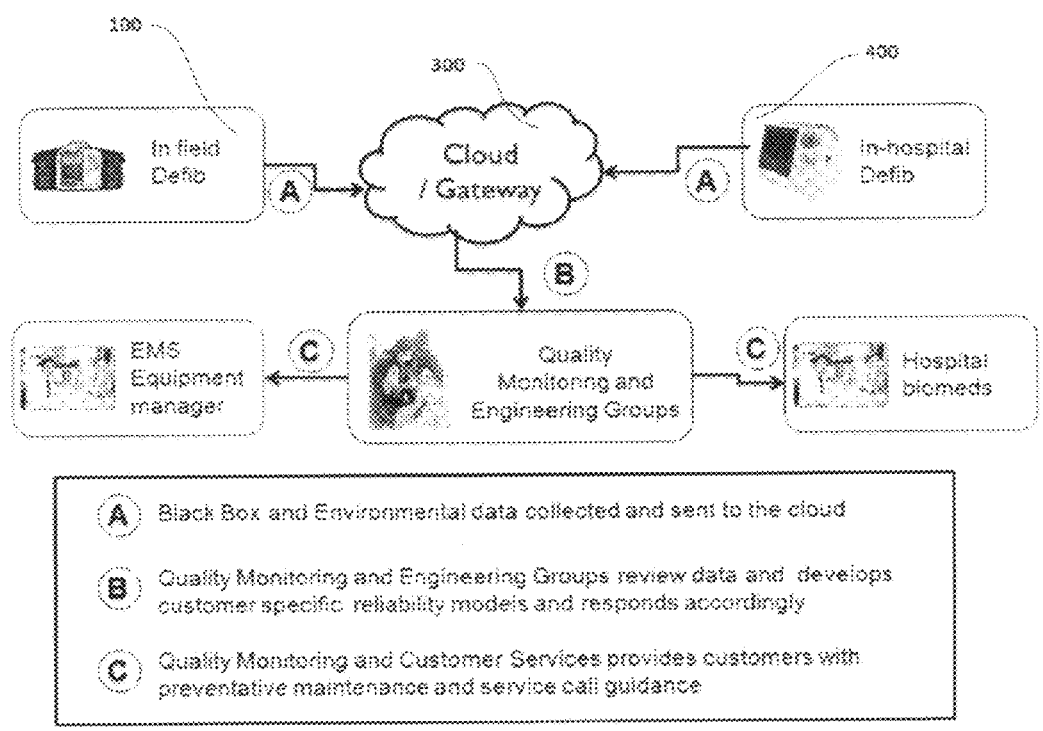
FIG. 5 illustrates another block diagram of the invention, illustrating the information flow between devices and the centralized functions, according to one embodiment of the invention.

FIG. 5 illustrates the utility of the networked system of FIG. 4. As illustrated there, devices and monitors 100 and 400 communicate via a cloud communication environment 300 to "Quality Monitoring and Engineering Groups" having a central computer 210. The monitoring and engineering groups are enabled by the invention to analyze the operating history and environment for the devices in real-time or near-real-time. The analysis output is preferably a predicted time to failure for each device, as well as the failure mode. In addition, the analysis output preferably provides supplemental preventive maintenance recommendations for each device customized to the environment/history. The recommendations may be changes to the scheduled self-testing, guidance for additional manual checks by the owner, requests to remove the device from service pending a visit from a service provider, or requests to return the device to the manufacturer for servicing. Each of these recommendations is preferably provided to customers such as "Hospital Biomeds" or "EMS Equipment Managers" prior to the actual failure of the device in the field.

The system may also be operable to compare the operating and environmental conditions of the device population to experiential failure rates. The comparison could subsequently be used by the manufacturer to develop specialized recommendations for use in new products, or to adjust a warranty package according to the particular user and/or region of the world which treats the device more harshly.

Figure 6:
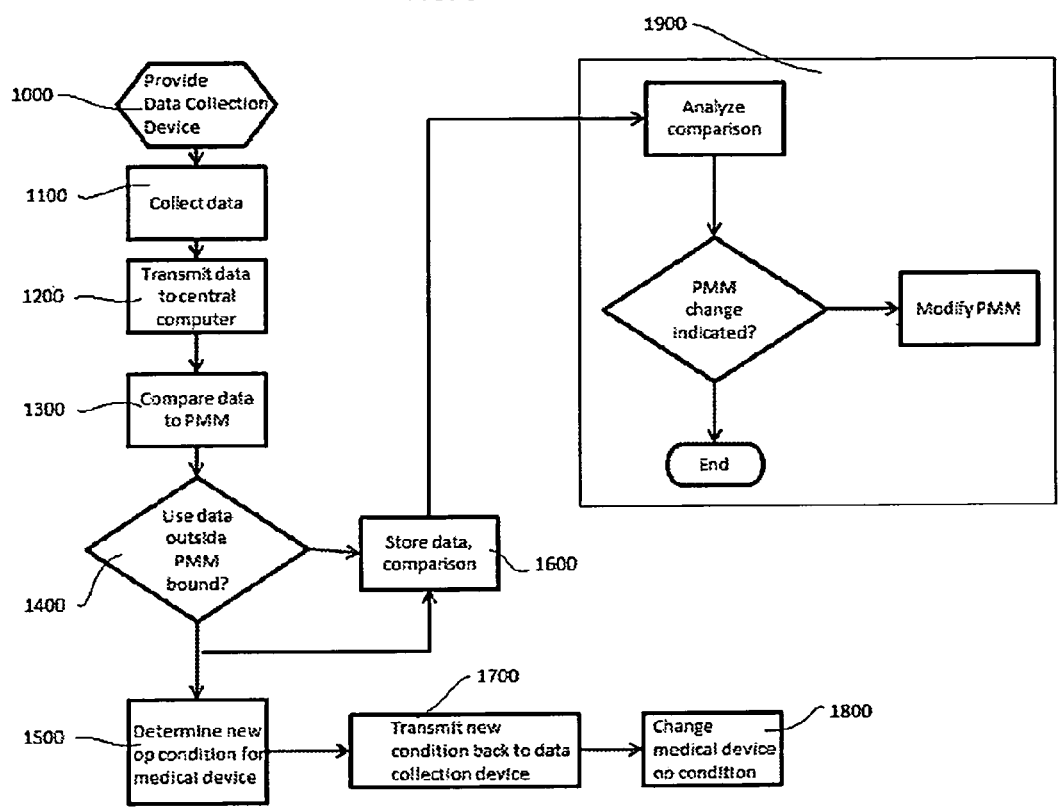
FIG. 6 illustrates a flow chart showing one embodiment of the inventive method.

FIG. 6 is a flow chart of a method for monitoring the use history of a medical device by comparing the use history to a preventive maintenance model (PMM). The method further provides a change to an operating condition of the medical device based on the comparison. The method, when applied to a plurality of devices, may further provide a change to the PMM upon which the comparison is based. The systems and apparatus as described previously act in concert to realize the benefits of the method.

The initial steps of the method provide one or more data collection devices at step 1000 which collect at step 1100 operational data and environmental data about the medical devices to which the data collection devices are attached. The data is transmitted at step 1200 to a central computer for analysis. At step 1300, the central computer compares the operational data and the environmental data with a predetermined PMM. The comparison may indicate that the underlying device is at risk, of impending (or premature) failure by determining that the data place the device history outside the bounding parameters of the PMM model. If so, decision step 1400 directs the method toward corrective action starting at step 1500. If the device is determined not to be at risk of premature failure, the data is stored at step 1600 for use in subsequent comparison with like devices or for refining the PMM.

Method step 1500 applies the data and comparison to the determination as to a modified or recommended operational condition for the device, for the purpose of ensuring that the device remains reliable and functional in the field. The types of modification, as described previously, could be changes to the scheduled self-testing, guidance for additional manual checks by the owner, requests to remove the device from service pending a visit from a service provider, or requests to return the device to the manufacturer for servicing. The guidance provided to the device owner could be conveyed by the step 1200 communication pathway at step 1700 or by conventional means such as telephone or mail communications. Responsive to the transmission of the new conditions to the data collection device, the underlying medical device operating condition is changed at step 1800. Preferably the change is completely automatic so that the user is not required to take further action.

Step 1900 enables the method to utilize the stored data and comparisons from a plurality of devices to refine the PMM. The comparisons, environmental data, and operational histories are analyzed, preferably with some additional data regarding actual failure rates and modes from devices. If the analysis indicates that the PMM should be refined or modified, the method does so.

The feedback and analysis enabled by the invention provide a better understanding of the actual use and abuse of the underlying device population. Such understanding leads to improved designs for the next generation of product. In addition, the understanding of different use profiles and environments for the product enables the manufacturer to customize preventive maintenance procedures and to better predict a time to failure for that particular device.

The feedback portion of the invention allows the manufacturer to identify those customers that subject their devices to harsh conditions. The manufacture can then remotely alert the customer to perform more frequent preventive maintenance. Also, the invention could alert manufacturer service personnel as to the particular devices which are more likely to require a service call. Finally, the manufacturer is in a better position to adjust warranty and other service-related costs according to the customer profile and/or region which demonstrate harsher treatment of the product.

Modifications to the device, software, and displays as described above are encompassed within the scope of the invention. For example, the method may be accomplished at the data collection device itself if the PPM and computer are resident there, thus eliminating the need for method steps 1200 and 1700. Thus, instead of transmitting environmental and use data from the monitor as often, the cloud communication path would periodically transmit updates to the PMM from the central computer to the data collection device population. Then the monitors would compare their own data against the resident PMM to adjust parameters or notify the user. When a particular monitor determines that it has departed by a certain amount from the PMM, then it could transmit the stored data back to the central computer, where the PMM is adjusted (using that data and data received from many other devices). The adjusted PMM is subsequently returned to the monitor as an update.

Also, the appearance and arrangement of the alerts at the device location may differ, in type and in appearance. Different maintenance models which are incorporated into the central computer, but which perform essentially the same predictive functions as described, also fall within the scope of the invention.

It should be understood that, while the present invention has been described in terms of medical applications, the teachings of the present invention are much broader and are applicable for non-medical applications and uses. Further, As one having ordinary skill in the art will appreciate in view of the teachings provided herein, features, elements, components, etc. described in the present disclosure/specification and/or depicted in the appended Figures may be implemented in various combinations of hardware and software, and provide functions which may be combined in a single element or multiple elements. For example, the functions of the various features, elements, components, etc. shown/illustrated/depicted in the Figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present invention can take the form of a computer program product accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk-read only memory (CD-ROM), compact disk-read/write (CD-R/W) and DVD. Further, it should be understood that any new computer-readable medium which may hereafter be developed should also be considered as computer-readable medium as may be used or referred to in accordance with exemplary embodiments of the present invention and disclosure.

Having described preferred and exemplary embodiments of systems, devices and methods in accordance with the present invention (which embodiments are intended to be illustrative and not limiting), it is noted that modifications and variations in/to such exemplary embodiments can be made by persons skilled in the art in light of the teachings provided herein (including the appended Figures). It is therefore to be understood that such changes which can be made in/to the preferred and exemplary embodiments of the present disclosure are within the scope of the present invention and the exemplary embodiments disclosed herein.

What is claimed is:

1. A data collection device for monitoring use history of a medical device, the medical device including a self-test circuit for sensing a fault in the medical device, the data collection device comprising:
    an environmental sensor that collects environmental data from a use environment of the medical device;
    a memory that records operating data of the medical device and the environmental data from the environmental sensor;
    a wireless transceiver that transmits the environmental data and the operating data to a remote memory; and
    a controller in communication with the medical device, the environmental sensor, the memory, and the transceiver, wherein the controller causes the transceiver to transmit the environmental data and the operating data to the remote memory, and further receives an instruction, through the wireless transceiver, for modifying a protocol for maintaining the medical device to more accurately predict and/or to avoid a fault in the medical device, as sensed by the self-test circuit,
    wherein the data collection device is attached to the medical device, and is co-located with the medical device in the use environment.

2. The data collection device of claim 1, wherein:
    the controller communicates the instruction to the medical device.

3. The data collection device of claim 2, further comprising a user output in communication with the controller, the user output providing preventive maintenance feedback corresponding to the instruction.

4. The data collection device of claim 1, further comprising a power supply that is independent of the medical device.

5. The data collection device of claim 1, wherein the operating data comprises at least one of button pushes, hardware logs, software logs, power fluctuations, charge times, and key patient parameter data.

6. The data collection device of claim 1, wherein the environmental data collected from the use environment of the medical device comprises at least one of temperature, humidity, condensation, shock, vibration, and location data.

7. A system for monitoring a use history of a medical device, the medical device having a self-test circuit for sensing a fault in the medical device, the system comprising:
    a data collection device, attached to the medical device having the self-test circuit, co-located with the medical device in a use environment, the data collection device comprising:
        an environmental sensor that collects environmental data from the use environment of the medical device, a memory recording operating data of the medical device and recording the environmental data from the environmental sensor, a wireless transceiver that transmits the environmental data and the operating data to a second memory, and a controller in communication with the medical device, the environmental sensor, the memory, and the transceiver, the controller causing the transceiver to transmit the environmental data and the operating data prior to a sensed fault in the medical device;

the second memory remote from the data collection device and in communication with the transceiver to receive and store the transmitted environmental data and the operating data; and a central computer in communication with the second memory, the central computer comparing the environmental data and the operating data against a predictive maintenance model, and predicting a time to failure of the medical device based on the comparison.

8. The system of claim 7, wherein the central computer further causes an alert to be transmitted to the data collection device corresponding to the prediction.

9. The system of claim 8, wherein the data collection device causes the medical device to adjust a parameter in the self-test circuit in response to the alert.

10. The system of claim 8, wherein the data collection device further comprises a user output to provide preventive maintenance feedback in response to the alert.

11. The system of claim 10, wherein the preventive maintenance feedback comprises an instruction to alter the medical device preventive maintenance protocol.

12. The system of claim 10, wherein the preventive maintenance feedback comprises an instruction to remove the medical device from service.

13. The system of claim 7, wherein the data collection device, the second memory, and the central computer are communicatively connected via a cloud communication environment.

14. The system of claim 7, further comprising:

a plurality of additional data collection devices attached to a plurality of additional medical devices, respectively, wherein the second memory receives and stores a set of environmental data and operating data received from each of the additional data collection devices, and wherein the central computer collects use histories of the data collection device and the plurality of additional data collection devices, and adjusts the predictive maintenance model based on the collected use histories.

15. The system of claim 7, wherein the central computer further characterizes the medical device in the use environment based on the comparison.

16. The data collection device of claim 1, wherein modifying the protocol for maintaining the medical device comprises adjusting an internal self-testing protocol of the self-test circuit in the medical device.

17. The data collection device of claim 16, wherein adjusting the internal self-testing protocol comprises adjusting a self-testing schedule to test the medical device more often.

* * * * *